United States Patent [19]

Nishimura

[11] 3,997,516

[45] Dec. 14, 1976

[54] METHOD FOR PROTECTING GUANIDINO GROUP AND RESTORING THE SAME

[75] Inventor: Osamu Nishimura, Osaka, Japan

[73] Assignee: Takeda Chemical Industries, Ltd., Osaka, Japan

[22] Filed: June 27, 1975

[21] Appl. No.: 590,948

[30] Foreign Application Priority Data

July 4, 1974 Japan ............................ 49-77117
Feb. 25, 1975 Japan ............................ 50-23664

[52] U.S. Cl. .................... 260/112.5 R; 260/470; 260/471 C; 260/515 M; 260/471 R; 260/534 R; 260/112.5 LH

[51] Int. Cl.$^2$ ............. C07C 103/52; C07C 149/40; C07C 63/00

[58] Field of Search .......... 260/112.5 R, 112.5 LH, 260/515 M, 518 R, 556 AR, 534 R, 470, 471 C, 471 R

[56] References Cited

UNITED STATES PATENTS 3,960,830   6/1976   Bayer et al. ................ 260/112.5 R

*Primary Examiner*—Lewis Gotts
*Assistant Examiner*—Reginald J. Suyat
*Attorney, Agent, or Firm*—Wenderoth, Lind & Ponack

[57] ABSTRACT

A guanidino group in an amino acid or a peptide can be protected with a specific protective group, i.e. lower alkoxybenzenesulfonyl group or tri-lower alkylbenzenesulfonyl group, and the protective group may easily be removed without affecting the amino acid or the peptide to be derived from the protected amino acid or peptide. Thus, the method is useful in the related chemical industries, especially in the peptide synthesis.

17 Claims, No Drawings

METHOD FOR PROTECTING GUANIDINO GROUP AND RESTORING THE SAME

This invention relates to a method for protecting the guanidino group

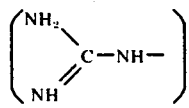

and restoring the same. More particularly, this invention concerns novel and useful amino acids and peptides having the guanidino group protected with a specific protective group, i.e. loweralkoxybenzenesulfonyl group or tri-lower alkylbenzenesulfonyl group.

As the protective group for the guandino group, the tosyl group, for instance, has frequently been employed particularly in the peptide synthesis. However, not only yield of the introduction of the tosyl group into the guandino group but also recovery of the guanidino group are not always satisfactory.

With the purpose for contemplating the improvements in those respects, the present inventor has made an extensive research and found that lower alkoxybenzenesulfonyl group and tri-lower alkylbenzenesulfonyl group are satisfactory ones for protecting the guandino group.

A principal object of the present invention is to provide amino acides and peptides having guandino groups protected with the specific protective group, i.e. lower alkoxybenzenesulfonyl group or tri-lower alkylbenzenesulfonyl group.

Another object of the present invention is to provide a novel method for protecting the guandino group in an amino acid or a peptide with said specific protective groups.

A further object of the present invention is to provide a method for restoring the guanidino group.

Other objects will become clear hereinafter as the disclosure proceeds.

The protection of the guandino group in the present invention may be realized through the introduction of the lower alkoxybenzenesulfonyl or the tri-lower alkylbenzenesulfonyl group into the guanidino group of the amino acid or peptide.

The lower alkoxyl group of the lower alkoxybenzenesulfonyl group to be introduced into the guanidino group may preferably have one to three carbon atoms and may be, for example, methoxy, ethoxy, propoxy and isopropoxy. Those groups may be attached to any position of the benzene ring and preferably to the 4-position relative to the sulfonyl group. More specific examples of those groups may be p-mehtoxybenzenensulfonyl (hereinafter may be abbreviated to "MBS"), p-ethoxybenzenesulfonyl, p-propoxybenzenesulfonyl and p-isopropoxybenzenesulfonyl.

The lower alkyl groups of the tri-lower alkylbenzenesulfonyl group to be introduced into the guanidino group may be the same or different from each other and may have preferably one to five carbon atoms and may be, for example, methyl, ethyl, propyl, isopropyl, n-butyl, t-butyl, n-amyl and t-amyl. Those groups may be attached to any positions of the benzene ring and preferably to the 2,4- and 6-positions relative to the sulfonyl group.. More specific examples of the tri-lower alkylbenzenesulfonyl groups are 2,4,6-trimethylbenzenesulfonyl, 2,4,6-triethylbenzenesulfonyl, 2.4.6-tripropylbenzenesulfonyl, 2.4.6-triisopropylbenzenesulfonyl and 2,4,6-tri-t-butylbenzenesulfonyl.

Protection of the guanidino group with those protective groups may be carried out by any of convenient processes for introducing substituted benzene-sulfonyl group into the guanidino group. And, typical example of such a process may be reacting a conventional reactive derivative, e.g. halogenides such as chlorides, fluorides, bromides and iodides, of the benzenesulfonic acid with a guanidino group-containing starting material. The reaction of this exemplified process may preferably be conducted in the presence of a base. The base may be, for example, sodium hydroxide, potassium hydroxide and lithium hydroxide, and is used generally in an amount of about 1 to 10 equivalents, preferably about 1 to 5 equivalents relative to one equivalent of the guanidino group-containing starting material. The reaction may preferably be conducted in a suitable solvent (e.g. acetone, dioxane, dimethylformamide or tetrahydrofuran). Reaction temperature ranges generally from about −10° C to 25° C and preferably from about −5° C to 10° C.

The protective group may be introduced into the guanidino group.

The guanidino group-containing amino acid or peptide whose guanidino group thus protected may be subjected to some conventional chemical modifications, e.g. synthetic reactions for obtaining another amino acid or peptide. Thereafter, if required, the protective group may easily be removed to restore the guanidino group. The removal of the protective groups may easily be carried out with less sidereactions by per se conventional procedures, for instance, by the use of Lewis acids (e.g. boron tristrifluoroacetate (may be abbreviated to "BTFA"), mineral acid (e.g. anhydrous hydrogen fluoride)). In this connection, the present inventor has found that lower alkylsulfonic acids (e.g. methanesulfonic acid, trifluoromethanesulfonic acid, or ethanesulfonic acid) or halogenosulfonic acids (e.g. fluorosulfonic acid) are more advantageously used for the removal of the protective groups. Those acids may be served also as solvents for the removal step. The removal reaction may be carried out in a solvent (e.g. trifluoroacetic acid, acetic acid, chloroform or methylene chloride). Reaction temperature may range generally from −5° C to about 50° C.

The present method for protection and restoration of the guanidino group is effectively applicable to any chemical reactions employing amino acids and peptides so far as those contain guanidino group or groups, either in liquid or solid phase reaction, irrespective of configurations of the amino acids of peptides.

The present method has the following technical advantages:

1. The present protective groups are introduced into the guanidino group in a good yield of over about 70 percent, as compared with yield of about 40 percent in the case of the known protective tosyl group.

2. Recovery of the guanidino group may reach completion, as compared with about twenty percent in the tosyl group.

3. Cleavage of the present protective group proceeds more rapidly than that of the tosyl group.

Throughout the present specification and the claims, abbreviations are used for designating amino acids, peptides and their activating or protective groups, and activating and protecting agents of amino acids or peptides according to those of IUPAC-IUB Commision on Biological Nomenclature or to those commonly used in this particular field of the art.

Examples of the abbreviations are as follows:

Ala: Alanine
Arg: Arginine
Asn: Asparagine
Asp: Aspartic acid
Gly: Glycine
Glu: Glutamic acid
His: Histidine
Leu: Leucine
Ileu: Isoleucine
Lys: Lysine
Met: Methionine Met: Methionine oxide (with =O)
Phe: Phenylalanine
Pro: Proline
p . Glu: Pyroglutamic acid
(Pyr)Glu: Pyroglutamic acid
Ser: Serine
Thr: Threonine
Trp: Tryptophan
Tyr: Tyrosine
Val: Valine
Bzl: Benzyl ether
BOC: t-Butyloxycarbonyl
BTFA: Borontristrifluoroacetate
DCC: N,N'-Dicyclohexylcarbodiimide
DC-urea: Dicyclohexyl urea
DCHA: Dicyclohexylamine
HONB: N-Hydroxy-5-norbornene-2,3-dicarboximide
NH$_2$Et: Ethylamine
OBzl: Benzyl ester
ODNP: 2,4-Dinitrophenyl ester
OEt: Ethyl ester
OMe: Methyl ester
ONBzl: p-Nitrobenzyl ester
ONB: HONB ester
O$^t$Bu: t-Butyl ester
Tos: Tosyl
Z: Benzyloxycarbonyl
OTcp: 2,4,5-Trichlorophenyl ester
Gln: Glutamine In the present specification and the claims, amino acids are of L-configurations unless otherwise specifically designated.

EXAMPLE 1

Each of tosylarginine (0.1 m mole) and p-methoxybenzenesulfonylarginine (0.1 m mole) is dissolved in trifluoroacetic acid (0.5 ml.). While each of the solutions is cooled at 0° C, 6, 8 or 10 equivalents of BTFA solution in trifluoroacetic acid is added. Each of the mixture is stirred at 0° C for one hour and diluted with 50 ml. of water. The mixture is lyophilized and the lyophilizate is subjected to amino acid analysis. The results are shown in the following Table.

Table 1

| Amount of BTFA | Recovery of arginine | | |
|---|---|---|---|
| | 6 equivalents | 8 equivalents | 10 equivalents |
| Tos<br>\|<br>H-Arg-OH | 1.3 % | 3.2 % | 11.2 % |
| MBS<br>\|<br>H-Arg-OH | 70.0 % | 82.0 % | 100 % |

EXAMPLE 2

Methanesulfonic acid (0.5 ml.) containing 5 % anisole is added to each of H-Arg(MBS)-OH(100 μ mole) and H-Arg (Tos)-OH (100 μ mole) and the mixtures are treated at 22° C for 40 minutes. The resulting oil is washed well with ether and then subjected to amino acid analysis. The results are shown in the following Table.

Table 2

| | Recovery of arginine |
|---|---|
| H-Arg(Tos)-OH | 23.4 % |
| H-Arg(MBS)-OH | 100 % |

EXAMPLE 3

1. Preparation of Z-Arg(MSS)-OH ("MSS" is abbreviation for "mesitylenesulfonyl," which may be used hereinafter)

Z-Arg-OH(3.08 g., 0.01 M) is dissolved in a mixture of 4N aqueous NaOH(10 ml.) and acetone (80 ml.) and the solution is cooled with ice. A solution of mesitylenesulfonyl chloride (4.38 g., 0.02 M) in acetone (10 ml.) is drowisely added to the solution in 10 minutes. The mixture is stirred for 2 hours and citric acid is added to make the solution acidic. The acetone is evaporated in vacuo and the oily residue is dissolved in ethyl acetate. The ethyl acetate layer is washed twice with water and extracted with 5 % aqueous NaHCO$_3$. The aqueous extract is made acidic with citric acid. The separating oily substance is extracted with ethyl acetate. The ethyl acetate layer is washed twice with water and concentrated to dryness in vacuo. The oily residue is triturated with petroleum benzin to yield powder. Yield, 4.0 g.(81.8 %), melting point: 110°–112° C(decomp.) [α]$_D^{23}$–0.41°(c=0.97, methanol)

Elemental analysis: C$_{23}$H$_{28}$O$_6$N$_4$S:
Calculated: C, 56.54; H, 5.78; N, 11.47; S, 6.56.
Found: C, 56.28; H, 6.10; N, 10.96; S, 6.39.

2. Preparation of H-Arg(MSS)-OH

Z-Arg(MSS)-OH(2.0 g.) is dissolved in methanol and hydrogenated over palladium black. The catalyst is removed by filtration and the filtrate is concentrated to dryness. Ethyl acetate is added to the residue and the resulting powder is collected by filtration. Yield, 1.3 g. (89.2 %) [α]$_D^{23}$–3.37°(c=0.89, methanol), melting point: 144–146° C (decomp.)

Elemental analysis: C$_{15}$H$_{24}$O$_4$N$_4$S: Calcd.: C, 50.54; H, 6.79; N, 15.27; S, 9.00. Found: C, 50.39; H, 6.78; N, 14.89; S, 8.79.

3. Removal of the MSS group a. Removal with methanesulfonic acid

Methanesulfonic acid (0.5 ml.) containing 5 percent anisole is added to H-Arg(MSS)-OH (35.6 mg., 100 μ mole) and the mixture is treated at 22° C for 40 minutes. Ether is added to the reaction mixture. The resulting oily substance is washed well with ether and dissolved in water (10 ml.). A portion of the solution is subjected to amino acid analysis to show 78 percent of the content of arginine.

b. Removal with BTFA

In each of three flasks H-Arg(MSS)-OH(35.6 mg., 100 µ mole) is supplied and dissolved in trifluoroacetic acid (0.5 ml.). Under cooling at 0° C, 6, 8 and 10 equivalents of BTFA solutions in trifluoroacetic acid are respectively added to the solutions and the mixtures are stirred at 0° C for one hour. The solutions are diluted with 10 times of water and lyophilized. The lyophilizates are dissolved in water (10 ml) and a portion of the solution is subjected to amino acid analysis to give the results in the following Table.

Table 3

| | BTFA | | |
|---|---|---|---|
| | 6 equivalents | 8 equivalents | 10 equivalents |
| Recovery of Arginine | 71.0 % | 80.0 % | 91.0 % |

EXAMPLE 4

1. Preparation of Z-Arg(TPS)-OH ("TPS" is an abbreviation for "2,4,6-triisopropylbenzenesulfonyl," which may be used hereinafter)

Employing 2,4,6-triisopropylbenzenesulfonyl chloride, the object compound is prepared by a procedure similar to that in Example 3-(1). Yield, 78.0 %, $[\alpha]_D^{23}$ −0.54°(c=1.11, methanol), melting point: 130°–135° C Elemental analysis: $C_{29}H_{42}O_6N_4S$: Calcd.: C, 60.60; H, 7.37; N, 9.72; S, 5.58. Found: C, 61.20; H, 7.41; N, 8.68; S, 5.70.

2. Preparation of H-ARG(TPS)-OH

The object compound is prepared by a procedure similar to that of Example 3-(2). Yield, 82.0 %, $[\alpha]_D^{22}$ −3.8°(c=1.02, methanol), melting point: 225°–226° C(decomp.).

Elemental analysis: $C_{21}H_{36}O_4N_4S \cdot \frac{1}{2}H_2O$: Calcd.: C, 56.10; H, 8.07; N, 12.46; S, 7.13. Found: C, 56.12; H, 8.24; N, 12.04; S, 7.21.

3. Removal of the TPS group a. Removal with methanesulfonic acid

Methanesulfonic acid (0.5 ml.) containing 5 % anisole is added to H-Arg(TPS)-OH (44.0 mg., 100 µ mole) and the mixture is treated at 22° C for 40 minutes. Ether is added to the reaction mixture and the resulting oily substance is washed well with ether. The oily substance is dissolved in water (10 ml.) and a portion of the solution is subjected to amino acid analysis to show 89.6 percent of content of arginine.

B. REMOVAL WITH BTFA

H-Arg(TPS)-OH(44.0 mg., 100 µ mole) is put in each of three flasks and dissolved in trifluoroacetic acid. Under cooling the solutions at 0° C, 6, 8 and 10 equivalents of BTFA solutions in trifluoroacetic acid are added. The mixture is stirred at 0° C for 1 hour and diluted with ten times of water. The solution is lyophilized and the lyophilizate is dissolved in water (10 ml.). A portion of the solution is subjected to amino acid analysis to give the results in the following Table.

Table 4

| | BTFA | | |
|---|---|---|---|
| | 6 equivalents | 8 equivalents | 10 equivalents |
| Recovery of arginine | 69.0 % | 78 % | 90.0 % |

EXAMPLE 5

Production of BOC-Arg(MBS)-OH

H-Arg(MBS)-OH(2.76 g., 8 m mole) is dissolved in a mixture of water (4.4 ml.) and triethylamine (1.68 ml., 12 m mole).

To this solution is added t-butyl S-4,6-dimethylpyrimidine-2-ylthiocarbonate (2.1 g., 8.8 m mole) dissolved in dioxane (4.4 ml.).

After being stirred for 12 hours at room temperature, the reaction mixture is subjected to evaporation under reduced pressure to remove dioxane. The residual solution is diluted with water, washed with ethylacetate and then adjusted to pH 2 with 5N HCl.

The resulting oily residue is extracted with ethylcetate. The ethylacetate layer is washed with water and dried over anhydrous $Na_2SO_4$.

The solvent is evaporated in vacuo to dryness. The oily residue is triturated with petroleum ether and then purified by reprecipitation from ethylacetate-petroleum ether. Yield, 3.25 g.(91.3 %), melting point: 85.0°–92.0° C (decomp.) $[\alpha]_D^{23}$+1.19(c=1.1, methanol)

Elemental analysis: $C_{18}H_{28}O_7N_4S \cdot \frac{1}{2}CH_3COOC_2H_5$: Calcd.: C, 49,17; H, 6.60; N, 11.47; S, 6.56. Found: C, 49.17; H, 6.53; N, 12.04; S, 6.89.

EXAMPLE 6

Production of bradykinin

1. Preparation of Z-Arg(MBS)-OH·DCHA·CH₃CN

Z-Arg-OH(55.5 g., 0.18 M) is dissolved in a mixture of 4N NaOH(180 ml.) and acetone (1.3 l.) and the solution is cooled with ice. A solution of p-methoxybenzenesulfonyl chloride (74.4 g., 0.36 M) in acetone (300 ml.) is added dropwisely in 30 minutes and the mixture is stirred for 2 hours. The mixture is made acidic with citric acid and subjected to distillation under reduced pressure to evaporate the acetone. The oily residue is dissolved in ethyl acetate. The ethyl acetate layer is washed twice with water and extracted with 5 percent aqueous $NaHCO_3$. The aqueous extract is made acidic with citric acid and the resulting oily substance is extracted with ethyl acetate. The ethyl acetate layer is washed twice with water and subjected to distillation under reduced pressure to evaporate the solvent. The oily residue (86.0 g.) is dissolved in ethyl acetate (600 ml.) and dicyclohexylamine (36.0 ml., 0.18 M) is added. The mixture is left standing in a refrigerator to be crystalized. The crystals are collected by filtration and recrystallized twice from $CH_3CN$. Yield, 77.0 g.(61.1 percent), melting point: 110°–112.0° C(decomp.). $[\alpha]_D^{23}$+5.1°(c=1.35, methanol)

Elemental analysis: $C_{33}H_{49}O_7N_5S \cdot CH_3CN$: Calcd.: C, 59.98; H, 7.48; N, 11.99; S, 4.58. Found: C, 59.97; H, 7.74; N, 11.72; S, 4.59.

2. Preparation of H-Arg(MBS)-OH

Oily Z-Arg(MBS)-OH(2 g.) is dissolved in methanol and hydrogenated over palladium black. Methanol is evaporated and the oily residue is recrystallized from hot water. Yield, 900 mg.(63.0 percent), melting point: 144°–146.0° C (decomp.) $[\alpha]_D^{23}$ –6.1°(c=0.71, methanol)

Elemental analysis: $C_{13}H_{20}O_5N_4S\cdot\frac{1}{2}H_2O$: Calcd.: C, 44.18; H, 5.99; N, 15.85; S, 9.07. Found: C, 44.05; H, 5.80; N, 15.73; S, 8.99.

3. Preparation of Z-Arg(MBS)-ONBzl

Z-Arg(MBS)-OH·DCHA·CH₃CN (7.0 g., 0.01 M) is suspended in ethyl acetate and treated with 0.2N $H_2SO_4$(60 ml.) to be converted into Z-Arg(MBS)-OH. The ethyl acetate is evaporated and the oily residue is dissolved in dimethylformamide (30 ml.). Under cooling with ice, triethylmine (1.68 ml., 0.012 M) and p-nitrobenzyl bromide (2.59 g., 0.012 M) are added. The reaction mixture is stirred at 80° C for 2 hours and left standing at room temperature overnight. The mixture is poured into water and the aqueous mixture is extracted with ethyl acetate. The ethyl acetate layer is washed with 1N HCl and 5 percent $NaHCO_3$, dried over anhydrous $Na_2SO_4$ and subjected to distillation to evaporate the solvent. The oily residue is triturated with petroleum ether to give powder. Yield, 6.2 g.(100 percent), melting point: 90.0°–110.0° C(decomp.) $[\alpha]_D^{21}$ –3.4°(c=0.59, dimethylformamide)

Elemental analysis: $C_{28}H_{31}O_9N_5S$: Calcd.: C, 54.80; H, 5.09; N, 11.41; S, 5.23. Found: C, 55.49; H, 5.15; N, 11.15; S, 4.36.

Rf¹: 0.91(chloroform: methanol: acetic acid=9:1:0.5) The same solvent system is used hereinafter with respect to Rf¹.

4. Preparation of Z-Phe-Arg(MBS)-ONBzl z-Arg(MBS)-ONBzl(6.1 g., 0.01 M) is treated with 25 percent HBr in acetic acid at room temperature for 40 minutes. The resulting powder is collected by filtration, dried in a desiccator over NaOH overnight and dissolved in dimethylformamide (30 ml.). To this solution is added triethylamine (2.8ml.,0.02 M) under ice-cooling and the formed salt is removed by filtration. Z-Phe-ONB (4.6 g., 0.01 M) is added to the filtrate and the mixture is stirred at room temperature overnight. The reaction mixture is diluted with water and extracted with ethyl acetate. The ethyl acetate layer is washed with 1N HCl and 5 % $NaHCO_3$, dried over anhydrous $Na_2SO_4$ and subjected to distillation to evaporate the solvent. The oily residue is triturated with petroleum benzin to yield crystals. The crystals are recrystallized from ethanol. Yield, 4.5 g.(59.2 %), melting point: 130.0°–132.0° C $[\alpha]_D^{21}$ –6.8°(c=0.66, dimethylformamide)

Elemental analysis: $C_{37}H_{40}O_{11}N_6S$: Calcd.: C, 58.41; H, 5.30; N, 11.05; S, 4.22. Found: C, 58.52; H, 5.19; N, 10.98; S, 4.36.

Rf¹=0.82

5. Preparation of BOC-Ser-Pro-Phe-Arg(MBS)-ONBzl

Z-Phe-Arg(MBS)-ONBzl(3.8 g., 0.005 M) is treated with 25 % HBr/acetic acid (20 ml.) at room temperature for 40 minutes. Ether is added and the resulting powder is collected. The powder is dried in a desiccator over NaOH overnight and dissolved in dimethylformamide (20 ml,). To this solution is added triethylamine (1.4 ml., 0.01 M) under ice-cooling and the formed salt is removed by filtration. In the filtrate are dissolved BOC-Ser-Pro-OH [melting point: 147.0°–148.0° C (decomp.)] (1.5 g., 0.005 M) and HONB (900 mg., 0.005 M), followed by addition of N,N'-dicyclohexylcarbodiimide. The mixture is stirred at 4° C for 2 days and further at room temperature for 1 day. After evaporation of the dimethylformamide, the residue is dissolved in ethyl acetate. The ethyl acetate solution is washed with 0.2 N Hcl and 5 % $NaHCO_3$ and dried over anhydrous $Na_2SO_4$. The ethyl acetate is evaporated and petroleum benzin is added to the residue. The resulting crystals are recrystallized from ethyl acetatepetroleum benzin. Yield 3.8 g.(83.4 %), melting point: 155°–160.0° C $[\alpha]_D^{21}$ –26.0° c=0.52, dimethylformamide)

Elemental analysis: $C_{42}H_{54}O_{13}N_8S\cdot\frac{1}{2}H_2O$: Calcd.: C, 54.83; H, 6.02; N, 12.18; S, 3.49. Found: C, 54.81; H, 6.00; N, 11.87; S, 3.53.

6. Preparation of BOC-Phe-Ser-Pro-Phe-Arg(MBS)-ONBzl

BOC-Ser-Pro-Phe-Arg(MBS)-ONBzl(3.64 g., 0.004 M) is treated with trifluoroacetic acid (30 ml.) at room temperature for 30 minutes. After evaporation of the trfluorocetic acid under reduced pressure, ether is added to the residue to give powder. The powder is dried in a desiccator over NaOH overnight and dissolved in dimethylformamide (20 ml.). To this solution is added triethylamine (0.56 ml., 0.004 M) under ice-cooling, followed by addition of BOC-Phe-ONB (1.72 g., 0.004 M). The mixture is stirred at room temperature for 6 hours and the dimethylformamide is evaporated in vacuo. The residue is dissolved in ethyl acetate. The solution is washed with 0.2 N HCl and 5 % $NaHCO_3$, dried over anhydrous $Na_2SO_4$ and subjected to distillation to evaporate the solvent. Ether is added to the residue and the mixture is filtered to obtain the crystals which are recrystallized from ethyl acetate. Yield, 4.0 g.(94.6 percent), melting point: 165.0°–170.0° C, $[\alpha]_D^{21}$ –22.2°(c=0.59, dimethylformamide)

Elemental analysis: $C_{15}H_{63}O_{14}S\cdot H_2O$: Calcd.: C, 56.92; H, 6.09; N, 11.71; S, 2.92. Found: C, 56.58; H, 5.76; N, 11.66; S, 3.17.

Rf¹=0.65

7. Preparation of Z-Arg(MBS)-Pro-Pro-Gly-O'Bu

Oily Z-Pro-Pro-Gly-O'Bu(4.9 g., 0.0106 M) (Rf¹=0.80) is dissolved in methanol (70 ml.) and subjected to catalytic hydrogenation over palladium black for 3 days. The catalyst is removed by filtration and the filtrate is concentrated to dryness. The oily residue is dissolved in a mixed solvent (100 ml.) of dioxane and tetrahydrofuran (9:1). To this are added and dissolved Z-Arg(MBS)-OH(prepared by the conventional procedure from Z-Arg(MBS)-OH·DCHA·CH₃CN (7.42 g., 0.0106 M)) and HONB (2.4 g., 0.0117 M) is added to the solution under ice cooling and the mixture is stirred at 4° C for 2 days. The formed DC-urea is removed by filtration and the filtrate is concentrated to dryness. The oily residue is dissolved in ethyl acetate and the solution is washed with 0.2 N HCl and 5 percent $NaHCO_3$ and dried over anhydrous $Na_2SO_4$. The ethyl acetate is evaporated in vacuo and the oily residue is triturated with ether. The resulting powder is reprecipitated rom ethyl acetate-ether. Yield, 5.5 g. 66.2 %), melting point: 120.0°–130.0° C(decomp.), $[\alpha]_D^{21}$ –47.7°(c=0.53, dimethylformamide)

Elemental analysis: $C_{37}H_{51}O_{10}N_7S\cdot\frac{1}{2}H_2O$: Calcd.: C, 55.90; H, 6.59; N, 12.33; S, 4.03. Found: C, 55.89; H, 6.62; N, 12.31; S, 4.05.
Rf$^1$=0.70

8. Preparation of Z-Arg(MBS)-Pro-Pro-Gly-OH

Z-Arg(MBS)-Pro-Pro-Gly-O$^t$Bu(4.72 g., 0.006 M)is is treated with trifluoroacetic acid (30 ml.) at room temperature for 30 minutes. The trifluoroacetic acid is evaporated in vacuo and the oily residue is dissolved in ehtyl acetate. The solution is washed twice with water and dried over anhydrous $Na_2SO_4$. The ethyl acetate is evaporated and the residue is triturated with ether. The resulting powder is collected by filtration and purified by reprecipitation from ethyl acetate. Yield, 3.5 g.(85.4 percent), melting point: 80.0°–90.0° C(decomp.), $[\alpha]_D^{21}$–46.4°(c=0.56, dimethylformamide)

Elemental analysis: $C_{33}H_{43}O_{10}N_7S\cdot H_2O$: Calcd.: C, 53.00; H, 6.06; N, 13.11; S, 4.29. Found: C, 53.13; H, 6.03; N, 12.60; S, 4.26.
Rf$^1$=0.44

9. Preparation of Z-Arg(MBS)-Pro-Pro-Gly-Phe-Ser-Prp-PheArg(MBS)-ONBzl

BOC-Phe-Ser-Pro-Phe-ARg(MBS)-ONBzl(1.06 g., 1 mM) is dissolved in cold trifluoroacetic acid (12 ml.) and the solution is left standing at room temperature for 30 minutes. 5.85 N Hcl is dioxane (0.17 ml.) is added to the solution and the trifluoroacetic acid is evaporated. Ether is added to the oily residue to give powder. The powder is collected by filtration and dried over NaOH in desiccator overnight and dissolved in dimethylformamide (20 ml.). The solution is neutralized with 10 percent solution (1.28 ml.) of N-ethylmorpholine in dimethylformamide under cooling. Z-Arg(MBS)Pro-Pro-GLy-OH(730 mg., 1 mM) and HONB (270 mg., 1.5 mM) are added to and dissolved in the solution, and N,N'-dicyclohexylcarbodiimide (247 mg., 1.2 mM) is added. The mixture is stirred at 4° C for 3 days and further at room temperature for 1 day. The formed DC-urea is removed by filtration and the dimethylformamide is evaporated from the filtrate. The residue is washed with ether by decantation and recrystallized three times from hot ethanol. Yield, 1.4 g.(84.0 percent), melting point: 120.0°–125.0° C(decomp.) $[\alpha]_D^{22}$–37.1°(c=0.56, dimethylformamide) Rf$^2$=0.06 (ethyl acetate:pyridine:acetic acid:water=60:20:6:11)

Elemental analysis: $C_{79}H_{96}O_{21}N_{16}S_2\cdot 2H_2O$: Calcd.: C, 55.62; H, 5.91; N, 13.14; S, 3.76. Found: C, 55.62; H, 5.87; N, 12.97; S, 3.87. Amino acid analysis (6 N HCl,110° C, 24 hours) Arg, 1.94(2); Ser. 0.96(1); Pro,3.08(3); Gly, 0.96(1); Phe, 1.98(2), Average recovery, 98.0 %

10. Preparation of H-Arg(MBS)-Pro-Pro-Gly-Ser-Pro-Phe-Arg(MBS)-OH

Z-ARG(MBS)-Pro-Pro-Gly-Phe-Ser-Pro-Phe-Arg(MBS)ONBzl(4.0 g., 2.4 mM) is dissolved in 80 percent aqueous acetic acid solution (100 ml) and subjected to catalytic hydrogenation over palladium black for 8 hours. The catalyst is removed by filtration and the residue is concentrated in vacuo. The oily residue is triturated with acetone-ether (1:1) and the resulting powder is washed well with hot acetone. Yield, 3.4 g.(100 percent), melting point: 170.0°–180.0° C(decomp.) $[\alpha]_D^{24}$–51.3°(c=0.50, acetic acid)

Elemental analysis: $C_{64}H_{85}O_{17}N_{15}S_2\cdot H_2O$: Calcd.: C, 54.19; H, 6.18; N, 14.81; S, 4.52. Found: C, 54.16; H, 6.35; N, 14.76; S, 4.58. Amino acid analysis (6N HCl, 110° C, 24 hours):
Arg, 2.07(2); Ser, 0.93(1); Pro, 2.90(3); Gly, 1.00(1);
Phe, 1.95(2), Average recovery, 100 percent 11. Preparation of H-Arg-Pro-Pro-Gly-Phe-Ser-Pro-Phe-Arg-OH(i.e. bradykinin) by removal of the MBS group with methanesulfonic acid H-Arg(MBS)-Pro-Pro-Gly-Phe-Ser-Pro-Phe-Arg(MBS)-OH(280 mg., 0.2 mM) is dissolved in a mixture of anisole (0.12 ml.) and methanesulfonic acid (3.0 ml.) and the mixture is stirred at room temperature for 40 minutes. Ether is added and the resulting oily substance is taken by decantation. The oily substance is washed well with ether and dissolved in water. The solution is passed through a column (2.5 × 10 cm) of Amberlite IRA-410(acetate form) to carry out ion exchange. The effluents are pooled and lyophilized. Yield, 233 mg.

The obtained powder is dissolved in water and the solution is poured into a column (2.5 × 12.0 cm) of carboxymethylcellulose, which is washed with 0.01 N ammonium acetate. Elution is carried out by the linear gradient method with 0.01 N ammonium acetate (500 ml.) and 0.3 N ammonium acetate (500 ml.). The desired fractions are pooled and lyophilized. Yield, 178 mg. Purification is repeated by the same conditions. Yield, 170 mg. $[\alpha]_D^{24}$–80.8°(c=0.49, water) Amino acid analysis (6N HCl, 110° C, 24 hours): Arg, 2.03(2); Ser, 0.96(1); Pro, 3.03(3); Gly, 1.00(1); Phe, 2.02(2), Average recovery, 94.3 percent Paper electrophoresis: pH 1.9(acetate buffer) - 4.2 cm Thin layer chromatography:
Rf=0.11(solvent; ethyl acetate:n-butanol:acetic acid:water = 1:1:1:1)
Rf=0.72(solvent; n-butanol:pyridine:acetic acid:water = 30:20;6:24)

EXAMPLE 7

Production of angiotensin converting enzyme inhibitor of the formula (Pyr)Glu-Trp-Pro-Arg-Pro-Gln-Ileu-Pro-Pro-OH 1. Preparation of Z-Ileu-Pro-Pro-O$^t$Bu Z-Pro-Pro-O$^t$Bu(11.6 g., 0.03 M) is hydrogenated over palladium black in methanol for 8 hours and the catalyst is removed by filtration. Reaction is carried out in dioxane (80 ml.) at 80° C for 7 hours between H-Pro-Pro-O$^t$Bu which is prepared by concentrating the filtrate, and Z-Ileu-ONB which is prepared by condensing Z-Ileu-OH(7.96 g., 0.03 M) with HONB (5.40 g., 0.03 M), and DCC (6.19 g., 0.03 M). The dioxane is evaporated and the residue is dissolved in ethyl acetate. The solution is washed with 5 percent aqueous NaHCO$_3$ and 0.2N HCl. After evaporation of the ethyl acetate, the oily residue is purified by column-chromatography on silica gel with chloroform. Yield, 12.0 g.(77.4 percent) (oily substance).

2. Preparation of Z-Gln-Ileu-Pro-Pro-O$^t$Bu

Z-Ileu-Pro-Pro-O$^t$Bu(12.0 g., 0.0233 M) is hydrogenated over palladium black in methanol for 8 hours. The resulting H-Ileu-Pro-Pro-O$^t$Bu (6.5 g., 0.0233 M) and HONB (4.17 g., 0.0233M) are dissolved in dimethylformamide (50 ml.) and DCC (4.81 g., 0.0233 M) is added to the solution under cooling at 0° C. The mixture is stirred for 12 hours. The formed BC-urea is removed by filtration and the filtrate is diluted with water, followed by extraction with ethyl acetate. The ethyl acetate layer is washed with 0.2 N HCl and 5 percent aqueous NaHCO$_3$, dried and distilled to evaporate the ethyl acetate. Petroleum benzin is added to the oily residue to yield crystals. The crystals are collected by filtration and dissolved in ethyl acetate. N,N-Dimethylaminopropylamine (2.5 ml.) is added to the solution and the mixture is left standing for 3 hours. The ethyl acetate layer is washed with 0.2N HCl and the ethyl acetate is evaporated. The residue is triturated with petroleum benzin. The resulting powder is collected by filtration and recrystallized from ethanol. Yield 3.8 g. (25.3 percent), melting point: 98°–100° C, $[\alpha]_D^{21}$–82.2°(c=0.69, dimethylformamide)

Elemental analysis: $C_{33}H_{49}O_8N_5 \cdot \frac{1}{2}H_2O$: Calcd.: C, 60.72; H, 7.72; N, 10.73. Found: C, 60.38; H, 7.57; N, 10.69.

3. Preparation of Z-Arg(MBS)-Pro-O$^t$Bu

Z-Pro-O$^t$Bu (10.0 g., 0.03 M) is hydrogenated over palladium black by the conventional procedure to prepare H-Pro-O$^t$Bu. In dioxane (50 ml.) are dissolved H-Pro-O$^t$Bu prepared above, Z-Arg(MBS)-OH which is prepared from Z-Arg(MBS)-OH.DCHA.CH$_3$CN (21.0 g., 0.03 M), and HONB (5.4 g., 0.03 M), DCC (6.2 g., 0.03 M) is added and the mixture is stirred for 48 hours in a cold room of 4° C. The formed DC-urea is removed by filtration and the filtrate is distilled to evaporate the dioxane. The residue is dissolved in ethyl acetate. The solution is washed with 5 percent aqueous NaHCO$_3$ and 0.2 N HCl, dried and distilled to evaporate the ethyl acetate. The residue is triturated with petroleum benzin and the resulting crystals are recrystallized twice from 50 percent ethanol. Yield, 13.0 g.(69.0 percent), melting point: 137°–139° C $[\alpha]_D^{21}$–28.0°(c=0.53, dimethylformamide)

Elemental analysis: $C_{30}H_{41}O_8N_5S$: Calcd.: C, 57.04; H, 6.54; N, 11.09; S, 5.07. Found: C, 56.70; H, 6.67; N, 11.20; S, 5.10.

4. Preparation of Z-Pro-Arg(MBS)-Pro-O$^t$Bu

Z-Arg(MBS)-Pro-O$_t$Bu (12.6 g., 0.02 M) is hydrogenated in methanol for 16 hours by the conventional procedure. H-Arg(MBS)-Pro-O$^t$Bu prepared above and Z-Pro-ONB (8.2 g., 0.02 M) are dissolved in dioxane (100 ml.) and the solution is stirred at room temperature for 3 hours. Dioxane is evaporated and the residue is dissolved in ethyl acetate. The solution is washed with 5 percent aqueous NaHCO$_3$ and 0.2N HCl, dried and distilled to evaporate the ethyl acetate. The residue is triturated with ether and the resulting powder is reprecipitated from ethyl acetate-ether. Yield, 12.3 g.(84.2%), melting point: 90°–95° C(decomp.), $[\alpha]_D^{21}$–55.2°(c=0.54, dimethylformamide)

Elemental analysis: $C_{35}H_{49}O_9N_6S$: Calcd.: C, 57.60; H, 6.77; N, 11.52; S, 4.39. Found: C, 57.40; H, 6.77; N, 11.30; S, 4.27.

5. Preparation of Z-Trp-Pro-Arg(MBS)-Pro-O$^t$Bu

Z-Pro-Arg(MBS)-Pro-O$^t$Bu (11.7 g., 0.016 M) is dissolved in methanol and hydrogenated by the conventional procedure. In dioxane (150 ml.) are dissolved H-Pro-Arg(MBS)-Pro-O$^t$Bu prepared above, Z-Trp-ONB prepared from Z-Trp-OH (5.4 g., 0.016 M), HONB (2.9 g., 0.016 M) and DCC (3.3 g., 0.016 M). The solution is stirred at room temperature for 12 hours. The dioxane is evaporated in vacuo and the residue is dissolved in ethyl acetate. The ethyl acetate layer is washed with 5 percent aqueous NaHCO$_3$ and 0.2N HCl and dried. The ethyl acetate is evaporated and the residue is triturated with ether. The resulting powder is dissolved in ethyl acetate, followed by addition of N,N-dimethylamino-propylamine (1 ml.). The mixture is left standing for one hour and the ethyl acetate layer is washed with 0.2N HCl. After evaporation of ethyl acetate, the residue is triturated with ether to collect the resulting powder by filtration. Yield, 11.5 g.(79.0 percent), melting point: 120°–125° C(decomp.) $[\alpha]_D^{21}$–53.5°(c=0.54, dimethylformamide)

Elemental analysis: $C_{46}H_{58}O_{10}N_8S \cdot \frac{1}{2}H_2O$: Calcd.: C, 50.79; H, 6.43; N, 12.13; S, 3.47. Found: C, 59.73; H, 6.37; N, 11.90; S, 3.43.

6. Preparation of (Pyr)Glu-Trp-Pro-Arg(MBS)-Pro-OH

Z-Trp-Pro-Arg(MBS)-Pro-O$^t$Bu(9.15 g., 0.01 M) is hydrogenated in methanol by the conventional procedure. The resulting H-Trp-Pro-Arg(MBS)-Pro-O$^t$Bu, (Pyr)Glu-OH(1.29 g., 0.01 M) and HONB (1.79 g., 0.01 M) are dissolved in dimethylformamide (30 ml.). DCC (2.06 g., 0.01 M) is added at 0° C and the mixture is stirred at room temperature for 12 hours. The formed DC-urea is removed by filtration and the dimethylformamide is evaporated in vacuo. Water is added and the resulting oily substance is taken by decantation. The oily substance is dissolved in ethanol and water is added. The resulting oily substance is taken again by decantation. The oily substance is dissolved in ethanol and ethyl acetate is added. The resulting powder is dissolved in trifluoroacetic acid (80 ml.) containing thioglycolic acid (1 ml.) and anisole (4 ml.) and the solution is left standing at room temperature for 40 minutes. Most of the trifluoroacetic acid is evaporated in vacuo and the residue is triturated with ether to collect the resulting powder by filtration. Yield, 7.8 g.(83.3 percent), melting point: 130°–135° C (decomp.), $[\alpha]_D^{21}$–29.2°(c=0.60, dimethylformamide)

Elemental analysis: $C_{39}H_{49}O_{10}N_9S$: Calcd.: C, 53.72; H, 6.12; N, 14.46; S, 3.68. Found: C, 53.68; H, 5.84; N, 13.93; S, 3.40.

7. Preparation of (Pyr)Glu-Trp-Pro-Arg(MBS)-Pro-Glu-Ileu-Pro-Pro-O$^t$Bu

Z-Gln-Ileu-Pro-Pro-O$^t$Bu(1.29 g., 0.002 M) is subjected to the conventional catalytic hydrogenation in methanol under the presence of one equivalent of hydrochloric acid. The resulting H-Gln Ileu-Pro-Pro-O$^t$Bu·HCl, Pyr(Glu)-Trp-Pro-Arg(MBS)-Pro-OH (1.67 g., 0.002 M), HONB (537 mg., 0.003 M) and N-ethylmorpholine (0.26 ml., 0.002 M) are dissolved in dimethylformamide (15 ml.). DCC (495 mg., 0.0024 M) is added at 0° C and the mixture is stirred at 4° in a cold room for 12 hours and at room temperature for 3 days. The formed DC-urea is removed by filtration and the filtrate is concentrated to dryness. The residue is triturated with ether and the resulting powder is purified by columnchromatography on silica gel (3.0 × 22.0 cm) with a solvent system (ethyl acetate:pyridine:acetic acid-water=60:20:6:11, the solvent system may be hereinafter referred to as "Rf$^2$"). Yield, 2.2 g. (83.0 percent), melting point: 175°–178° (decomp.) $[\alpha]_D^{24}$ –68.1°(c=0.56, dimethylformamide)

8. Preparation of (Pyr)Glu-Trp-Pro-Arg-Pro-Gln-Ileu-Pro-Pro-OH by removal of the MBS group with methanesulfonic acid Pyr(Glu)-Trp-Pro-Arg(MBS)-Pro-Gln-Ileu-Pro-Pro-O'Bu (266 mg.) is dissolved in a mixture of anisole (0.12 ml.), -thioglycolic acid (0.03 ml.) and methanesulfonic acid (3.0 ml.). The solution is stirred at room temperature for 30 minutes and ether is added. The resulting oily substance is taken by decantation and washed well with ether. The oily substance is dissolved in water and the solution is passed through a column (2.5 × 12.0 cm) of Amberlite IRA- 410(acetate form) to conduct ion exchange. 1N Ammonium acetate (20 ml.) is added to the effluent and the mixed solution is applied to a column (2.5 × 10.0 cm) of Amberlite XAD-2, which is washed with 0.01 N ammonium acetate (100 ml.). Elution is carried out by the linear gradient elution method with 0.01 N ammonium acetate (500 ml.) and 50 percent ethanol (500 ml.) containing 0.5 percent acetic acid. Yield 130 mg.

The obtained product is dissolved in 0.01 N ammonium acetate and the solution is passed through a column (2.5 × 10 cm) of carboxymethyl-cellulose. The effluent is pooled and lyophilized. Yield, 125 mg. $[\alpha]_D^{24}$ –160.4°(c=0.48, water) Amino acid analysis (6N HCl, 110° C, 24 hours):

Arg, 1.02(1), Trp, 0.90(1); Glu, 2.10(2); Pro, 3.96(4); Ileu, 1.02(1), Average recovery, 91.0 percent Thin layer chromatography Rf=0.67 (Solvent system; n-butanol:pyridine:acetic acid:water=30:20:6:24)

8'. Preparation of (Pyr)Glu-Trp-Pro-Arg-Pro-Gln-Ilue-Pro-Pro-OH by removal of the MBS group with fluorosulfonic acid (Pyr)Glu-Trp-Pro-Arg(MBS)-Pro-Gln-Ileu-Pro-Pro-O'Bu (266 mg) is dissolved in a mixture of anisole (0.12 ml.), thioglycollic acid (0.03 ml.) and fluorosulfonic acid (3.0 ml.). The solution is stirred at room temperature for 30 minutes and ether is added. The separating oily substance is taken by decantation, washed well with ether and dissolved in water. The solution is passed through a column (2.5 × 12.0 cm) of Amberlite IRA-410(acetate form) to effect an ion exchange. 1N Ammonium acetate (120 ml.) is added to the effluent and the mixture is applied to a column (2.5 × 10.0 cm) of Amberlite XAD-2, which is washed with 0.01 N ammonium acetate (100 ml.). Elution is carried out by the linear gradient method with 0.01 N ammonium acetate (500 ml.) and 50 percent ethanol (500 ml.) containing 0.5 percent acetic acid. Yield, 130 mg.

The obtained substance is dissolved in 0.01 N ammonium acetate and the solution is passed through a column (2.5 × 10 cm) of carboxymethyl-cellulose. The effluent is pooled and lyophilized. Yield, 125 mg. $[\alpha]_D^{23}$ –159.3°(c=0.60, water) Amino acid analysis (6N HCl, 110° C, 24 hours):

Arg, 1.01(1); Trp, 0.89(1); Glu, 1.98(2); Pro, 4.00(4); Ileu, 1.00(1), Average recovery, 90.2percent Thin layer chromatography Rf=0.67 (Solvent; n-butanol: pyridine:acetic acid:water=30:20:6:24)

8". Preparation of (Pyr)Glu-Trp-Pro-Arg-Pro-Gln-Ileu-Pro-Pro-OH by removal of the MBS group with borontris trifluoroacetate (Pyr)Glu-Trp-Pro-Arg(MBS)-Pro-Glu-Ileu-Pro-Pro-O'Bu (266 mg., 0.2 mM) is dissolved in 30 ml. of trifluoroacetic acid and the solution is treated with 75 equivalents of BTFA at 0° C for 1 hour. The trifluoroacetic acid is evaporated in vacuo and the residue is dissolved in water (100 ml.) and the insolubles are removed by filtration. The filtrate is lyophilized and the lyophilizate is dissolved in a small amount of water. The solution is subjected to ion exchange on a column (2.0 × 10.0 cm) of Amberlite IRA-410 (acetate form). Ammonium acetate (1.5 g.) is added to the effluent (200 ml.) and the mixture is applied to a column (2.5 × 14.0 cm) of Amberlite XAD-2, which is washed with 0.01 M ammonium acetate (100 ml.). Elution is carried out by the exponential gradient elution method with 0.01 M ammonium acetate (1000 ml.) and 50 percent ethanol (1000 ml.) containing 0.5 percent acetic acid. The desired fractions are pooled and the ethanol is evaporated. The residue is lyophilized and the powdery lyophilizate is dissolved in water. The solution is passed through a column (2.0 × 7.5 cm) of carboxymethyl-cellulose. The desired fractions are pooled and lyophilized. Yield, 130 mg. $[\alpha]_D^{21}$ –152.8°(c=0.19, water) Amino acid analysis (6N HCl, 110° C, 24 hours): Arg, 1.02(1); Trp, 0.94(1); Glu, 2.04(2); Pro, 3.98(4); Ileu, 1.00(1), Average recovery, 92.0 percent

EXAMPLE 8

Production of GnRH [i.e. (Pyr)Glu-His-Trp-Ser-Tyr-Gly-Leu-Arg-Pro-Gly-NH₂]

1. Preparation of Z-Arg(MBS)-Pro-OH a. In dioxane (100 ml.) is dissolved Z-Arg(MBS)-OH which is prepared from Z-Arg(MBS)-OH·DCHA·CH₃CN (14.0 g., 0.02 M), and HONB (4.0 g., 0.022M) is added. Under cooling DCC (4.33 g., 0.021M) is added and the mixture is stirred at 4° C overnight. The formed DC-urea is removed by filtration. The filtrate is combined with a solution of H-Pro-OMe[prepared from H-Pro-OMe·HCl (4.98g., 0.03M) and triethylamine (4.2 ml., 0.03 M)] in DMF (100 ml.) and the mixture is stirred at room temperature for two days. After evaporation of the dioxane, the residual DMF is diluted with water and the resulting oil is extracted with ethyl acetate. The ethyl acetate layer is washed with 5 percent aqueous sodium hydrogen carbonate and with 0.2N HCl, followed by addition of N,N-dimethylamino-propylamine (2.5 ml.). The mixture is left standing for one hour. The ethyl acetate layer is washed with 1N HCl and dried over anhydrous sodium sulfate. Evaporation of the ethyl acetate yeilds an oily substance (10 g.).

The oily substance is dissolved in methanol (100 ml.) and 1N NaOH (50 ml.) is added. The mixture is left standing at room temperature for 4 hours. An adequate amount of crystals of citric acid is added to make the mixture acidic and the methanol is removed by evaporation. The oily residue is extracted with ethyl acetate. The ethyl acetate layer is washed with water, dried and subjected to distillation in vacuo. The oily residue is purified by columnchromatography on silica gel (solvent: chloroform, column: 6.0 × 15.0 cm). The desired fractions are pooled and concentrated. The residue is triturated with ether to yield the desired compound as powder. Yield 3.5 g.(30.5percent), melting point: 90.0°–93.0° C(decomp.) $[\alpha]_D^{23}$–27.5(c=0.59, methanol)

Elemental analysis: $C_{26}H_{33}O_8N_5S\cdot H_2O$: Calcd.: C, 52.60; H, 5.94; N, 11.80; S, 5.40. Found: C, 52.64; H, 5.56; N, 11.21; S, 5.43.

b. In trifluoroacetic acid is dissolved Z-Arg(MBS)-Pro-O$^t$Bu (400 mg.) and the solution is left at room temperature for 45 minutes. After evaporation of most of the trifluoroacetic acid, the oily residue is dissolved in ethyl acetate. The ethyl acetate layer is washed with water and dried. After evaporation of the ethyl acetate in vacuo, the oily residue is triturated with ether to yield powder. Yield 310 mg., melting point: 93.0°–95.0° C, $[\alpha]_D^{23}$–29.2°(c=0.55, methanol)

Elemental analysis: $C_{26}H_{33}O_8N_5S\cdot H_2O$: Calcd.: C, 52.60; H, 5.94; N, 11.80; S, 5.40. Found: C, 52.64; H, 5.56; N, 11.69; S, 5.17.

2. Preparation of Z-Arg(MBS)-Pro-Gly-NH$_2$

Z-Arg(MBS)-Pro-OH (3.45 g., 6 mM) and HONB (1.29 g., 7.2 mM) are dissolved in dioxane, and DCC (1.36 g., 6.6 mM) is added under cooling. The mixture is stirred for 5 hours and the formed DC-urea is removed by filtration, H-Gly-NH$_2$ (740 mg., 10 mM) is added to the filtrate and the mixture is stirred overnight. The dioxane is evaporated and the oily residue is dissolved in ethyl acetate. The solution is washed with 5 percent NaHCO$_3$ and with 0.2N HCl and dried. The ethyl acetate is evaporated and the oily residue is triturated with petroleum benzin. The resulting powder is reprecipitated from ethyl acetate and petroleum benzin. Yield 2.8 g.(74.0%), melting point: 90°–95.0° C(decomp.) $[\alpha]_D^{23}$–19.2°(c=0.53, methanol)

Elemental analysis: $C_{28}H_{37}O_8N_7S$: Calcd.: C, 53.24; H, 5.90; N, 15.52; S, 5.08. Found: C, 53.95; H, 6.32; N, 14.97; S, 4.40.

3. Preparation of Z-Leu-Arg(MBS)-Pro-Gly-NH$_2$

Z-Arg(MBS)-Pro-Gly-NH$_2$(2.7 g., 0.0042 M) is dissolved in methanol(50 ml.) and subjected to catalytic hydrogenation over palladium black at room temperature for 8 hours. The methanol is evaporated and the oily residue is dissolved in dioxane (50 ml.). To this is added Z-Leu-ONB [prepared from Z-Leu-OH(11.11 g., 0.0042 M), HONB (752 mg., 0.0042 M) and DCC (866 mg., 0.0042 M)] and the mixture is stirred overnight. The dioxane is evaporated in vacuo and the oily residue is extracted with ethyl acetate-n-butanol (1:1). The organic layer is washed with 5 percent NaHCO$_3$ and with 0.2N HCl and dried. The solvent is evaporated and the residue is triturated with ether. The resulting powder is reprecipitated twice from ethyl acetate. Yield 2.2 g. (70.3 percent), melting point: 125.0°–130.0° C, $[\alpha]_D^{23}$–35.6°(c=0.57, methanol)

Elemental analysis: $C_{34}H_{49}O_9N_8S\cdot\frac{1}{2}H_2O$: Calcd.: C, 54.10; H, 6.68; N, 14.84; S, 4.25. Found: C, 54.18; H, 6.52; N, 14.68; S, 4.33. Amino acid analysis (6N HCl, 110° C, 24 hours):

Arg. 1.03(1); Pro, 1.00(1); Gly, 0.97(1); Leu, 0.93 (1), Average recovery: 98.0%

4. Preparation of (Pyr)Glu-His-Trp-Ser-Tyr-Gly-Leu-Arg(MBS)-Pro-Gly-NH$_2$

Z-Leu-Arg(MBS)-Pro-Gly-NH$_2$ (1.34 g., 1.8 mM) is dissolved in methanol (70 ml.) and subjected to catalytic hydrogenation over palladium black for 8 hours. The catalyst is removed by filtration and the filtrate is concentrated in vacuo. The oily residue is dried in a desiccator in vacuo overnight and dissolved in DMF (20 ml.). To this are added (Pyr)Glu-His-Trp-Ser-Tyr-Gly-OH(1.37 g., 1.8 mM) and HONB (645 mg., 3.6 mM) and the mixture is cooled to −10° C. DCC (743 mg., 3.6 mM) is added and the mixture is stirred overnight. The formed DC-urea is removed by filtration and the filtrate is distilled in vacuo. Acetonitrile is added to the residue. The resulting powder is collected by filtration and purified twice by reprecipitations from ethanol. Yield 1.78 g. (73.0%), melting point: 180–185° C(decomp.) $[\alpha]_D^{23}$–27.4°(c=1.07, DMF)

Elemental analysis: $C_{62}H_{81}O_{16}N_{17}S\cdot H_2O$: Calcd.: C, 54.33; H, 6.10; N, 17.38; S, 2.34. Found: C, 54.47; H, 6.23; N, 16.64; S, 2.27.

5. Preparation of (Pyr)Glu-His-Trp-Ser-Tyr-Gly-Leu-Arg-Pro-Gly-NH$_2$ (i.e. GnRH)

(Pyr)Glu-His-Trp-Ser-Tyr-Gly-Leu-Arg(MBS)-Pro-Gly-NH$_2$ (676 mg., 0.5 mM) is added to a mixture of methanesulfonic acid (7 ml.), anisole (0.5 ml.) and thioglycolic acid (0.05 ml.) and the mixture is stirred at room temperature for one hour. Ether is added and the resulting oily substance is washed with ether by decantation. The oily substance is dissolved in water (10 ml.) and the solution is passed through a column (2.5 × 10.0 cm) of Amberlite IRA-410 (acetate form). The effluent (200 ml.) is poured into a column (2.5 × 14.0 cm) of carboxymethylcellulose, which is eluted with 0.005M ammonium acetate (500 ml.). Elution is carried out by the linear gradient elution method [0.005M ammonium acetate (500 ml.) and 0.2 M ammonium acetate (500ml.)]. The desired fractions are pooled and applied to a column (2.5 × 12.0 cm) of Amberlite XAD-2. The column is washed with 0.005 M ammonium acetate (200 ml.) and eluted by the linear gradient method [0.005 M ammonium acetate (500 ml.) and 60 percent aqueous ethanol (500 ml.)]. The desired fractions are pooled and the ethanol is evaporated. The residue is lyophilized and the lyophilizate is dissolved in 0.1 M acetic acid. The solution is passed through a column (3 × 130 cm) of Sephadex LH-20, and the desired fractions are pooled and lyophilized. Yield 375 mg. $[\alpha]_D^{23}$–50.5°(c=0.49, 5% aqueous acetic acid) Amino acid analysis (6N HCl, 110° C, 24 hours): His, 0.96(1);

Arg, 0.96(1); Trp, 0.83(1); Ser, 0.89(1) Glu, 1.06(1);

Pro, 1.02(1); Gly, 2.06(2), Leu, 1.00(1); Tyr, 1.00(1)

Average recovery: 89.0%

The compound shows chemical and biological properties identical with its authentic sample.

EXAMPLE 9

Production of tuftsin

1. Preparation of Z-Pro-Arg(MBS)-OH

H-Arg(MBS)-OH(2.76 g., 8 mM) is dissolved in DMF (15 ml.), followed by addition of triethylamine (1.12 ml. 8 mM) under cooling and by further addition to Z-Pro-ONB (3.28 g., 8 mM). The mixture is stirred at room temperature for 6 hours. Acetic acid (1.5 ml.) is added to the mixture and the DMF is evaporated in vacuo. The oily residue is dissolved in ethyl acetate and the ethyl acetate layer is washed three times with water. The ethyl acetate is evaporated in vacuo. The oily residue is triturated with ether and reprecipitated from chloroform-ether. Yield 3.9 g. (85.0%), melting point: 80.0°–85.0° C(decomp.) $[\alpha]_D^{24}$ –16.3°(c=0.58, DMF)

Elemental analysis: $C_{26}H_{33}O_8N_5S\cdot\frac{1}{2}H_2O$: Calcd.: C, 53.41; H, 5.86; N, 12.00; S, 5.49. Found: C, 53.37; H, 5.78; N, 11.66; S, 5.20.

2. Preparation of BOC-Lys(Z)-Pro-Arg(MBS)-OH

Z-Pro-Arg(MBS)-OH(3.46 g., 6 mM) is dissolved in a mixture (100 ml.) of methanol, water and acetic acid (6:3:1) and is subjected to catalytic hydrogenation over palladium black for 8 hours. The catalyst is removed and the filtrate is concentrated in vacuo. Water is added to the residue and the water is evaporated in vacuo. This procedure is repeated three times to remove acetic acid. The residue is dissolved in DMF (10 ml.), followed by addition of triethylamine (0.84 ml., 6 mM) and BOC Lys(Z)-OTcp (3.36 g., 6 mM). The mixture is stirred at room temperature for 12 hours. Acetic acid (2 ml.) is added and the DMF is evaporated in vacuo.

The residue is dissolved in ethyl acetate. The ethyl acetate layer is washed with water three times, dried and subjected to distillation in vacuo to evaporate the ethyl acetate. The residue is purified by column chromatography on silica gel [column: 6.0 × 6.0 cm, solvent; chloroform: methanol (97:3)]. Yield 3.4 g. (70.9 percent), melting point: 103.0°–109° C(decomp.), $[\alpha]_D^{24}$ –19.4°(c=0.70, DMF)

Elemental analysis: $C_{37}H_{53}O_{11}N_7S\cdot\frac{1}{2}H_2O$: Calcd.: C, 54.67; H, 6.69; N, 12.06; S, 3.95. Found: C, 54.72; H, 6.70; N, 11.78; S, 3.80.

3. Preparation of Z-Thr-Lys(Z)-Pro-Arg(MBS)-OH

Boc-Lys(Z)-Pro-Arg(MBS)-OH (1.86 g., 2.3 mM) is dissolved in trifluoroacetic acid (10 ml.) and the solution is stirred at 10° C for 20 minutes. Most of the trifluoroacetic acid is evaporated in vacuo and ether is added. The resulting precipitate is collected by filtration and dried. The product is dissolved in DMF (10 ml.), followed by addition of triethylamine (0.64 ml., 4.6 mM) under cooling with ice and further addition of Z-Thr-ONB (952 mg., 2.3 mM). The mixture is stirred at room temperature overnight. Acetic acid (2 ml.) is added and the DMF is evaporated in vacuo. Ether is added to the oily residue. The resulting powder is collected by filtration and reprecipitated from ethyl acetate-ether. Yield 2.1 g. (95.5%), melting point: 90.0°–95.0° C(decomp.), $[\alpha]_D^{24}$ –15.3°(c=0.62, DMF)

Elemental analysis: $C_{44}H_{58}O_{13}N_8S$: Calcd.: C, 56.28; H, 6.23; N, 11.93; S, 3.42. Found: C, 55.99; H, 6.22; N, 11.56; S, 3.36.

4. Preparation of H-Thr-Lys-Pro-Arg-Oh (i.e. tuftsin)

Z-Thr-Lys(Z)-Pro-Arg(MBS)-OH (1.88 g., 2 mM) is treated with a mixture of anisole (1.0 ml.) and methanesulfonic acid (17 ml.) at room temperature for 45 minutes. Ether is added and the resulting oily substance is washed well with ether by decantation. The oily substance is dissolved in water (10 ml.) and the solution is passed through a column (2.5 × 10.0 cm) of Amberlite IRA-410 (acetate form). Effluent 200 ml.) is pooled and applied to a column (2.5 × 15.0 cm) of carboxymethylcellulose, which is washed with water (500 ml.). Elution is carried out by the linear gradient method [water (500 ml.) and 0.2 M ammonium acetate (500 ml.)]. The desired fractions are pooled and lyophilized. The lyophilizate is dissolved in 0.1 M acetic acid and the solution is passed through a column (3.0 × 130.0 cm) of Sephadex LH-20. The desired fractions are pooled and lyophilized. Yield 840 mg., $[\alpha]_D^{23}$ –60.2° (c=0.55 , 5% acetic acid) Amino acid analysis (6N HCl, 110° C, 24 hours):Lys, 1.01(10)

Arg, 1.00(1); Thr, 0.99(1); Pro, 1.06(1). Average recovery 100 percent

The obtained product shows strong activity of chemotaxis.

EXAMPLE 10

Production of H-Thr-Lys-Arg-OH

1. Preparation of BOC-LYs(Z)-Arg(MBS)-OH

H-Arg(MBS)-OH (2.76 g., 8mM) is dissolved in DMF (15 ml), followed by addition of triethylamine (1.12 ml.,) 8 mM) under cooling with ice and further addition of BOC-Lys(Z)-OTcp (4.48 g., 8 mM). The mixture is stirred at room temperature for 48 hours. Acetic acid (3 ml.) is added and the DMF is evaporated in vacuo. The oily residue is dissolved in ethyl acetate and the ethyl acetate layer is washed with water. The ethyl acetate is evaporated in vacuo and the residue is triturated with ether. The resulting powder is reprecipitated from acetonitrile-ether. Yield 4.8 g. (84.4 percent), melting point: 95.0°–100° C(decomp.) $[\alpha]_D^{24}$ –4.2°(c=0.69, DMF)

Elemental analysis: $C_{32}H_{46}O_{10}N_6S$: Calcd.: C, 54.38; H, 6.56; N, 11.89; S, 4.54. Found: C, 54.06; H, 6.49; N, 11.84; S, 4.48.

2. Preparation of Z-Thr-Kys(Z)-Arg(MBS)-OH

BOC-LYs(Z)-Arg(MBS)-OH (4.24 g., 6 mM) is dissolved in trifluoroacetic acid (30 mg.) and the solution is stirred at 10° C for 20 minutes. Most of the trifluoroacetic acid is evaporated in vacuo and ether is added. The resulting precipitate is collected by filtration and dried. The productis dissolved in DMF (20 ml.), followed by addition of triethylamine (1.68 ml., 12 mM) under cooling with ice and further addition of Z-Thr-ONB (2.49 g., 6 mM). The mixture is stirred at room temperature for 12 hours. Acetic acid (3 ml.) is added and the DMF is evaporated in vacuo. The oily residue is dissolved in ethyl acetate. The ethyl acetate layer is washed with water and subjected to distillation in vacuo to evaporate the ethyl acetate. The oily residue is triturated with ether and reprecipitated from ethyl acetate-ether. Yield, 4.7 g. (93.1%), melting point: 77°–82.0° C(decomp.) $[\alpha]_D^{24}$ ×0.9°(c=0.53, DMF)

Elemental analysis: $C_{39}H_{51}O_{12}N_7S$: Calcd.: C, 55.63; H, 6.11; N, 11.65; S, 3.81. Found: C, 55.30; H, 6.181 N, 11.55; S, 3.95.

3. Preparation of H-Thr-Lys-Arg-OH

Z-Thr-Lys(Z)-Arg(MBS)-OH (1.68 g., 2 mM) is treated with a mixture of anisole (1.0 ml.) and methanesulfonic acid (17.0 ml.) at room temperature for 45 minutes. Ether is added and the resulting oily substance is washed well with ether. The oily substance is dissolved in water (10 ml.) and the solution is passed through a column (2.5 ×10.0 cm) of Amberlite IRA-410 (acetate form). Effluent (200 ml.) is pooled and applied to a column (2.5 × 15.0 cm) of carboxymethylcellulose, which is washed with water (200 ml.). Elution is carried out by the linear gradient method [water (200 ml.) and 0.2 M ammonium acetate (500 ml.)].

The desired fractions are pooled and lyophilized. The lyophilizate is dissolved in 0.1 M acetic acid (10 ml.) and the solution is passed through a column (3.0 × 130.0 cm) of Sephadex LH-20. The desired fractions are pooled and lyophilized. Yield 773 mg., $[\alpha]_D^{23} \times 8.8°$ (c=0.55, 5% acetoc acid) Amino acid analysis (6N HCl,110 C, 24 hours):

Lys, 1.00(1); Arg. 1.03(1), Thr, 1.00(1)

Average recovery 100 percent

Preparations of polypeptides according to the present invention are schematically shown as follows:

1. Preparation of H-Thr-Pro-Arg-Lys-OH

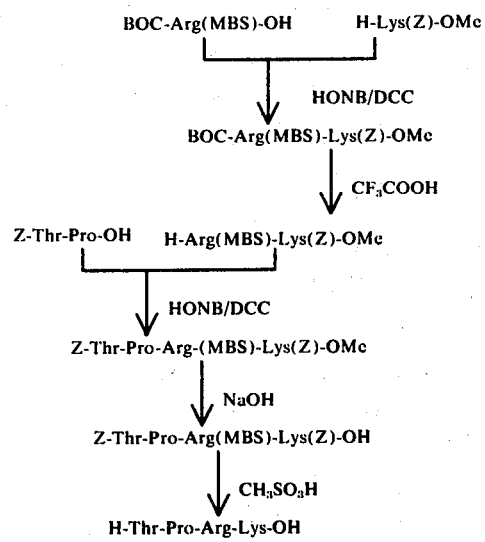

(2) Preparation of H-β-Ala-Arg-Gly-Phe-Phe-Tyr-NH₂
(a)

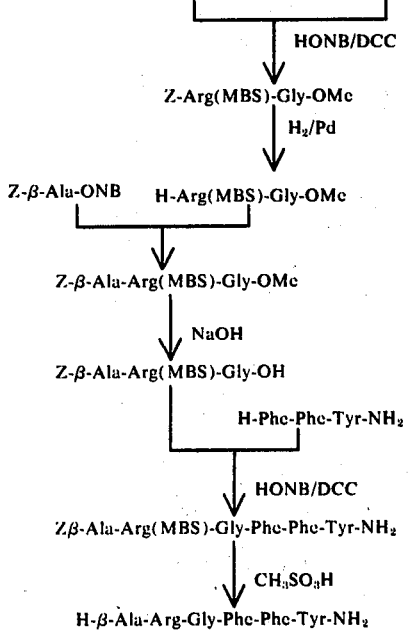

(b)
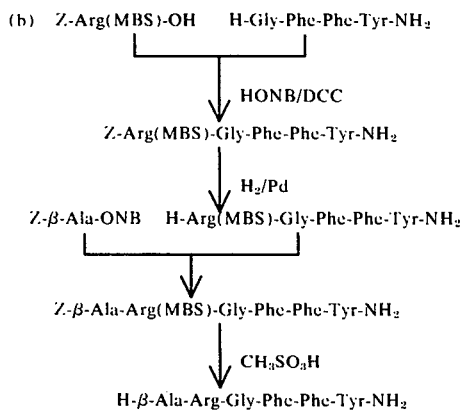
(3) Preparation of P . Glu-His-Trp-Ser-Tyr-D-Leu-Leu-Arg-Pro-NHEt
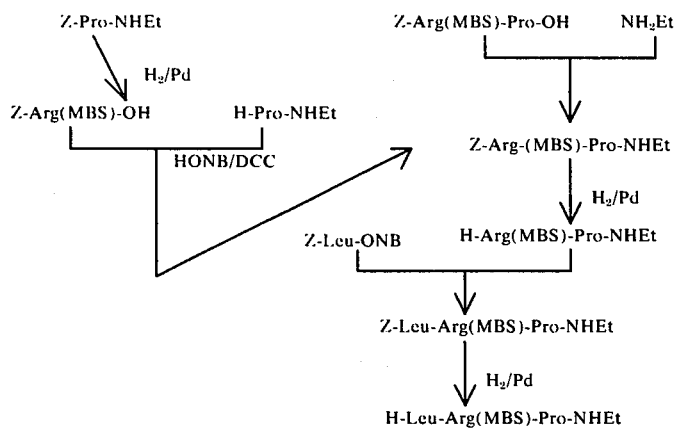
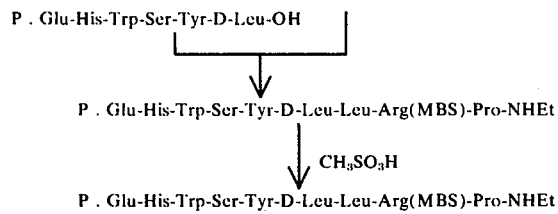
(4) Preparation of P . Glu-His-Trp-Ser-Tyr-D-Ala-Leu-Arg-Pro-NHEt
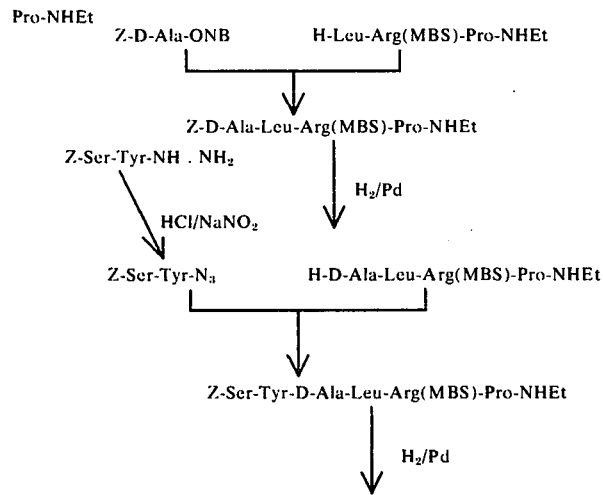

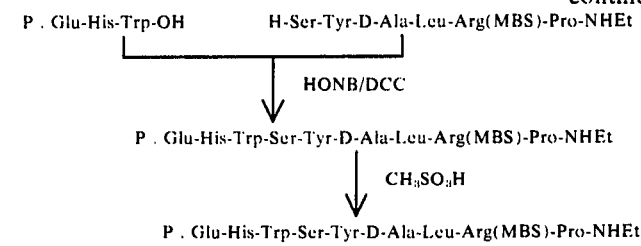
(5) Preparation of H-Ser-Tyr-Ser-Met-Glu-His-Phe-Arg-Trp-Gly-Lys-Pro-Val-Gly-Lys-Lys-Arg-Arg-Pro-Val-Lys-Val-Tyr-Pro-OH
[ACTH(1-24)]
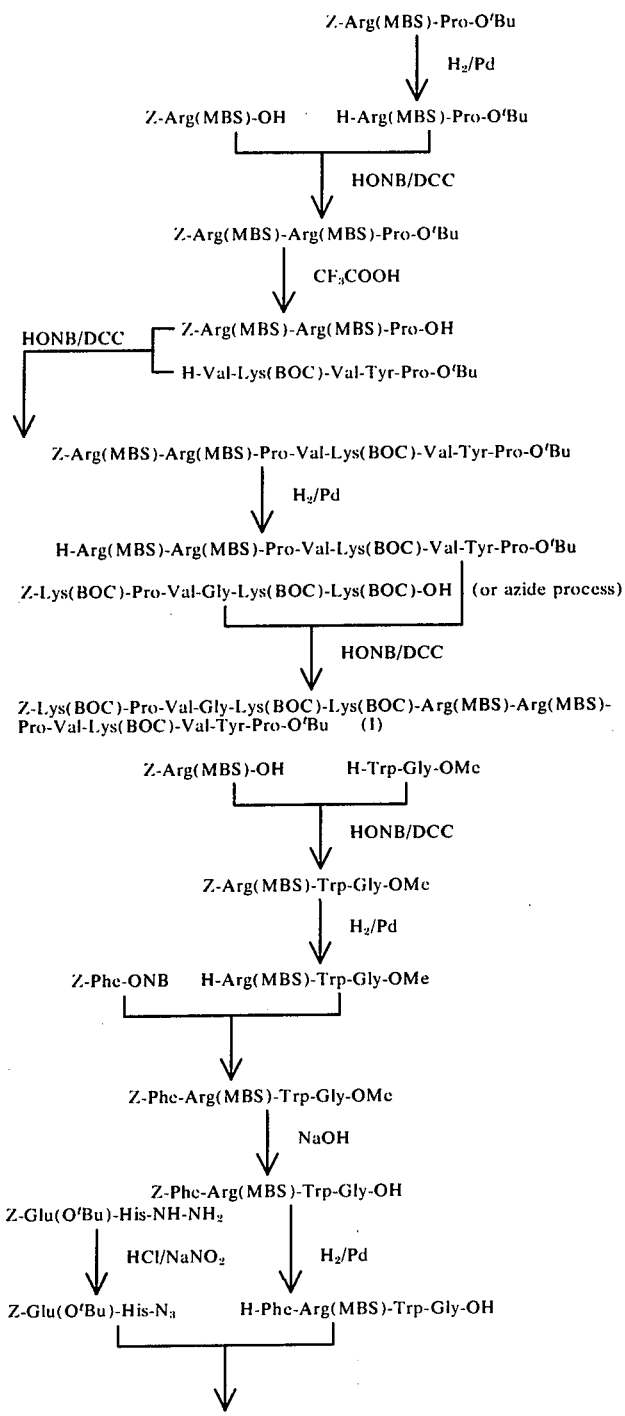

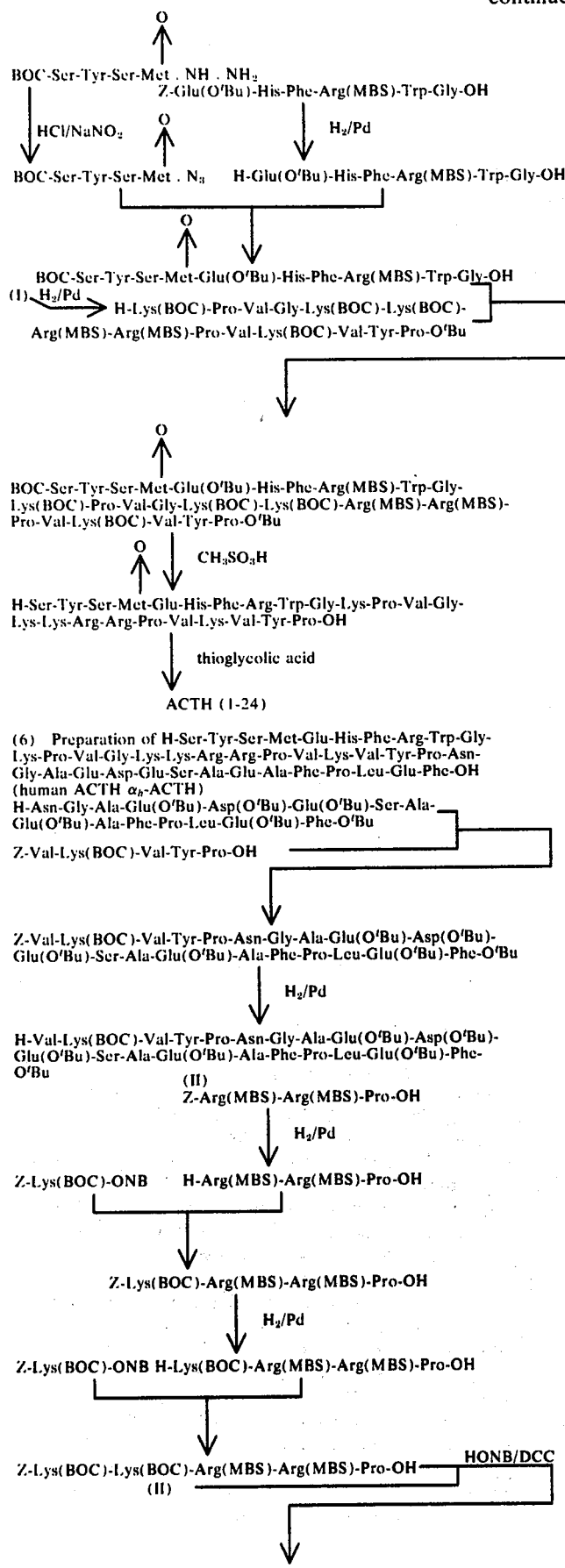

-continued

Z-Lys(BOC)-Lys(BOC)-Arg(MBS)-Arg(MBS)-Pro-Val-Lys(BOC)-Val-
Tyr-Pro-Asn-Gly-Ala-Glu(O'Bu)-Asp(O'Bu)-Glu(O'Bu)-Ser-Ala-
Glu(O'Bu)-Ala-Phe-Pro-Leu-Glu(O'Bu)-Phe-O'Bu

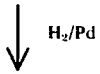 H₂/Pd

H-Lys(BOC)-Lys(BOC)-Arg(MBS)-Arg(MBS)-Pro-Val-Lys(BOC)-
Val-Tyr-Pro-Asn-Gly-Ala-Glu(O'Bu)-Asp(O'Bu)-Glu(O'Bu)-
Ser-Ala-Glu(O'Bu)-Ala-Phe-Pro-Leu-Glu(O'Bu)-Phe-O'Bu ⎤ HONB/DCC

Z-Lys(BOC)-Pro-Val-Gly-OH ─────────────────────────

Z-Lys(BOC-Pro-Val-Gly-Lys(BOC)-Lys(BOC)-Arg(MBS)-
Pro-Val-Lys(BOC)-Val-Tyr-Pro-Asn-Gly-Ala-Glu(O'Bu)-Asp(O'Bu)-
Glu(O'Bu)-Ser-Ala-Glu(O'Bu)Ala-Phe-Pro-Leu-Glu(O'Bu)-Phe-O'Bu

 H₂/Pd

H-Lys(BOC)-Pro-Val-Gly-Lys(BOC)-Lys(BOC)-Arg(MBS)-Arg(MBS)-
Pro-Val-Lys(BOC)-Val-Tyr-Pro-Asn-Gly-Ala-Glu(O'Bu)-
Asp(O'Bu)-Glu(O'Bu)-Ser-Ala-Glu(O'Bu)-Ala-Phe-Pro-Leu-
Glu(O'Bu)-Phe-O'Bu ⎤

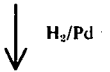

BOC-Ser-Tyr-Ser-Met-Glu(O'Bu)-His-Phe-Arg(HBS)-Trp-
Gly-OH ─────────────────────────────

HONB/DCC

BOC-Ser-Tyr-Ser-Met-Glu(O'Bu)-His-Phe-Arg(MBS)-Trp-Gly-Lys(BOC)-
Pro-Val-Gly-Lys(BOC)-Lys(BOC)-Arg(MBS)-Arg(MBS)Pro-Val-
Lys(BOC)-Val-Tyr-Pro-Asn-Gly-Ala-Glu(O'Bu)-Asp(O'Bu)-Glu(O'Bu)-
Ser-Ala-Glu(O'Bu)-Ala-Phe-Pro-Leu-Glu(O'Bu)-Phe-O'Bu

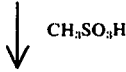 CH₃SO₃H

H-Ser-Tyr-Ser-Met-Glu-His-Phe-Arg-Trp-Gly-Lys-Pro-Val-Gly-Lys-
Lys-Arg-Arg-Pro-Val-Lys-Val-Tyr-Pro-Asn-Gly-Ala-Glu-Asp-Glu-
Ser-Ala-Glu-Ala-Phe-Pro-Leu-Glu-Phe-OH

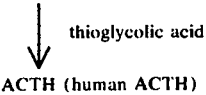 thioglycolic acid

α_h-ACTH (human ACTH)

What is claimed is:
1. In an amino acid having a protected guanidino group or a peptide containing the residue of an amino acid having a protected guanidino group the improvement according to which the protective grouping is a lower alkoxybenzenesulfonyl group or a tri-lower alkylbenzenesulfonyl group.

2. An amino acid or peptide as claimed in claim 1, wherein the amino acid is arginine.

3. An amino acid or peptide as claimed in claim 1, wherein the lower alkoxybenzenesulfonyl group is of one to three carbon atoms.

4. An amino acid or peptide as claimed in claim 1, wherein the lower alkoxybenzenesulfonyl group is the methoxybenzenesulfonyl group.

5. An amino acid or peptide as claimed in claim 1, wherein the lower alkoxybenzenesulfonyl group is the p-methoxybenzenesulfonyl group.

6. An amino acid or peptide as claimed in claim 1, wherein the tri-lower alkylbenzenesulfonyl group is of one to five carbon atoms.

7. An amino acid or peptide as claimed in claim 1, wherein the tri-lower alkylbenzenesulfonyl group is the tri-methylbenzenesulfonyl group.

8. An amino acid or peptide as claimed in claim 1, wherein the tri-lower alkylbenzenesulfonyl group is the 2,4,6-tri-methylbenzenesulfonyl group.

9. An amino acid or peptide as claimed in claim 1, wherein the tri-lower alkylbenzenesulfonyl group is the 2,4,6triisopropylbenzenesulfonyl group.

10. An amino acid or peptide as claimed in claim 1, wherein the tri-lower alkylbenzenesulfonyl group is the 2,4,6,-triisopropylbenzenesulfonyl group.

11. A peptide as claimed in claim 1, wherein the peptide is bradykinin.

12. A peptide as claimed in claim 1, wherein the peptide is of the formula (Pyr)Glu-Trp-Pro-Arg-Pro-Gln-Ileu-Pro-Pro-OH.

13. A peptide as claimed in claim 1, wherein the peptide is luteinizing hormone-releasing hormone.

14. A peptide as claimed in claim 1, wherein the peptide is tuftsin.

15. A peptide as claimed in claim 1, wherein the peptide is of the formula H-Thr-Lys-Arg-OH.

16. In a method for producing an amino acid having a protected guanidino group or a peptide containing the residue of an amino acid having a protected guanidino group which comprises reacting an amino acid or peptide containing a guanidino group with a reactive derivative of a compound capable of introducing the protective grouping into the guanidino group the improvement according to which the reactive derivative is a reactive derivative of lower alkoxybenzenesulfonic acid or tri-lower alkylbenzenesulfonic acid.

17. A method according to claim 16 wherein the protective grouping introduced into the guanidino group is subsequently removed by reacting the amino acid or a peptide containing the protected guanidino group with lower alkyl sulfonic acid or halogenosulfonic acid.

* * * * *